(12) United States Patent
La Riviere et al.

(10) Patent No.: US 9,513,233 B2
(45) Date of Patent: Dec. 6, 2016

(54) COLOR X-RAY HISTOLOGY FOR MULTI-STAINED BIOLOGIC SAMPLE

(71) Applicant: THE UNIVERSITY OF CHICAGO, Chicago, IL (US)

(72) Inventors: Patrick La Riviere, Chicago, IL (US); Yuxin Steve Wang, Palatine, IL (US); Darin Clark, Durham, NC (US); Keith Cheng, Hummelstown, PA (US)

(73) Assignees: THE UNIVERSITY OF CHICAGO, Chicago, IL (US); THE PENN STATE RESEARCH FOUNDATION, University Park, PA (US); UCHICAGO ARGONNE, LLC, Chicago, IL (US)

( * ) Notice: Subject to any disclaimer, the term of this patent is extended or adjusted under 35 U.S.C. 154(b) by 103 days.

(21) Appl. No.: 14/354,855

(22) PCT Filed: Oct. 29, 2012

(86) PCT No.: PCT/US2012/062431
§ 371 (c)(1),
(2) Date: Apr. 28, 2014

(87) PCT Pub. No.: WO2013/063577
PCT Pub. Date: May 2, 2013

(65) Prior Publication Data
US 2014/0301528 A1    Oct. 9, 2014

Related U.S. Application Data

(60) Provisional application No. 61/553,066, filed on Oct. 28, 2011.

(51) Int. Cl.
*A61B 6/00* (2006.01)
*G01N 23/04* (2006.01)
(Continued)

(52) U.S. Cl.
CPC .............. *G01N 23/04* (2013.01); *B82Y 10/00* (2013.01); *G01N 23/046* (2013.01);
(Continued)

(58) Field of Classification Search
CPC ...... A61B 6/032; A61B 6/482; A61B 6/508; A61B 6/485; G01N 2223/6126; G01N 23/04; G01N 23/046; G01N 23/2251; G01N 23/223; G01N 2223/0766; G06T 19/00; G06T 2210/41; G21K 2201/061; G21K 2201/064; B82Y 10/00
USPC ........................................................ 378/5, 67
See application file for complete search history.

(56) References Cited

U.S. PATENT DOCUMENTS 6,087,665 A    7/2000   Hoffman et al.
6,208,709 B1   3/2001   Melen
(Continued)

FOREIGN PATENT DOCUMENTS

EP       1890137 A1       2/2008
WO   WO-2006/109233 A2   10/2006

OTHER PUBLICATIONS

International Preliminary Report on Patentability from PCT/US2012/062431 dated May 8, 2014.
(Continued)

*Primary Examiner* — Thomas R Artman
(74) *Attorney, Agent, or Firm* — Marshall, Gerstein & Borun LLP

(57) ABSTRACT

Systems and methods are provided for staining tissue with multiple biologically specific heavy metal stains and then performing X-ray imaging, either in projection or tomography modes, using either a plurality of illumination energies or an energy sensitive detection scheme. The resulting energy-weighted measurements can then be used to decompose the resulting images into quantitative images of the distribution of stains. The decomposed images may be false-colored and recombined to make virtual X-ray histology images. The techniques thereby allow for effective differentiation between two or more X-ray dyes, which had previously been unattainable in 3D imaging, particularly 3D imaging of features at the micron resolution scale. While techniques are described in certain example implementations, such as with microtomography, the techniques are scalable to larger fields of view, allowing for use in 3D color, X-ray virtual histology of pathology specimens.

33 Claims, 10 Drawing Sheets

(51) Int. Cl.
  *G01N 23/223*  (2006.01)
  *G06T 19/00*  (2011.01)
  *G01N 23/225*  (2006.01)
  *B82Y 10/00*  (2011.01)
  *A61B 6/03*  (2006.01)

(52) U.S. Cl.
  CPC ....... *G01N 23/223* (2013.01); *G01N 23/2251* (2013.01); *G06T 19/00* (2013.01); *A61B 6/032* (2013.01); *A61B 6/482* (2013.01); *A61B 6/508* (2013.01); *G01N 2223/0766* (2013.01); *G01N 2223/6126* (2013.01); *G06T 2210/41* (2013.01); *G21K 2201/061* (2013.01); *G21K 2201/064* (2013.01)

(56) References Cited

U.S. PATENT DOCUMENTS

| | | | |
|---|---|---|---|
| 7,634,052 B2 | 12/2009 | Grodzins et al. | |
| 7,656,996 B2* | 2/2010 | Harding | G01N 23/223 378/44 |
| 2006/0269043 A1* | 11/2006 | Heismann | A61B 6/032 378/62 |
| 2008/0089584 A1* | 4/2008 | VanMetter | A61B 6/463 382/173 |
| 2009/0080600 A1 | 3/2009 | Keller et al. | |
| 2010/0290692 A1* | 11/2010 | Macaulay | G06T 7/0012 382/133 |
| 2010/0322494 A1 | 12/2010 | Fauver et al. | |
| 2012/0264110 A1* | 10/2012 | Wachman | G01N 33/57411 435/5 |

OTHER PUBLICATIONS

International Search Report from PCT/US2012/062431 dated Jan. 15, 2013.
O'Sullivan, "A Fast Sinc Function Gridding Algorithm for Fourier Inversion in Computed Tomography", IEEE Trans on Medical Imaging, vol. MI-4, No. 4, pp. 200-207 (1985).
Martin, et al. "LSO-Based Single Crystal Film Scintillator for Synchrotron-Based Hard X-Ray Micro-Imaging," IEEE Transactions on Nuclear Science, 56(3):1412-1418 (2009).
Metscher, "MicroCT for Developmental Biology: A Versatile Tool for High-Contrast 3D Imaging at Histological Resolutions," Developmental Dynamics 238:632-640 (2009).
Johnson, et al. "Virtual Histology of Transgenic Mouse Embryos for High-Throughput Phenotyping," PLoS Genetics 2(4):0471-0477 (2006).

* cited by examiner

COLOR X-RAY HISTOLOGY FOR MULTI-STAINED BIOLOGIC SAMPLE

CROSS REFERENCE TO RELATED APPLICATION

The present application claims the benefit of U.S. Provisional Application No. 61/553,066, entitled "Color X-Ray Histology for Multi-Stained Biologic Sample", filed on Oct. 28, 2011, which is hereby incorporated by reference herein in its entirety.

FIELD OF THE INVENTION

The invention generally relates to X-ray imaging and, more particularly, to a system for X-ray imaging using multiple illumination energies.

BACKGROUND

The background description provided herein and throughout the application is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

With the completion of genome projects for numerous model organisms, including mice, *drosophila,* and zebrafish, there is now a desire to link genes to structures and functions through systematic phenotyping of these model organisms. The work, called "phenome projects," is to be built on a foundation of anatomical and morphological information, supplemented with molecular, physiological, and behavioral assays.

Zebrafish, for example, are frequently used to provide non-mammalian model of human disease. Zebrafish offer various advantageous experimental features, including short generational time, fecundity, small size, transparency, and powerful genetic tools. The result is the creation of the "Zebrafish Phenome Project." The international zebrafish research community plans to generate at least one mutant for each gene, and each mutant will need to be phenotyped at multiple ages.

An ideal anato-morphological imaging assay would provide isotropic three-dimensional (3D) cellular resolution across an entire model organism, allowing for determination of cellular and tissue phenotypes arising from specific changes in the genotype. In order to phenotype thousands of mutants. Clearly, high-throughput processing would be needed.

Conventionally, two-dimensional glass and virtual histology slides are used in cellular-scale phenotyping of model organisms. But, with such techniques it is difficult to achieve true 3D information and high throughput. In classical histology, for example, mechanically sliced sections of fixed and wax-embedded tissue are cut into ~5 micrometer-thick sections, and stained with two different color dyes, hematoxylin and eosin, which stain different cellular components. From here, it is possible, in principle, to generate 3D representations by virtually stacking images obtained from the serial sections. However, the mismatch between histological slice thickness (typically 5 microns) and in-plane resolution (typically 200-500 nm) makes the generation of satisfactory 3D representations impractical. Moreover, the entire process of sectioning, staining, and imaging physical slices of the specimen is labor intensive. And as such, a truly 3D imaging modality would solve the problem of physically sectioning and virtually reassembling the specimen.

There are 3D imaging modalities, such as confocal microscopy, optical projection tomography, or magnetic resonance imaging, but they either lack the required 1-2 micron spatial resolution (MRI) or lack the ability to image in optically opaque whole specimens.

One modality that potentially offers an appealing combination of spatial resolution, penetration, and high throughput is X-ray computed tomography. Micro CT imaging is relatively fast, provides isotropic 3D images, permits virtual sectioning in any direction, and leaves the specimen intact for future imaging or sectioning.

The natural X-ray contrast of most model organisms is not sufficiently high to allow subtle phenotyping. But recently, a number of investigators have demonstrated that the use of single heavy-metal stains, of the kind used in electron microscopy, can be used to significantly increase contrast. Indeed some have recently made use of heavy-metal staining, along with synchrotron-based micro CT at ~1.4 micron resolution, to produce high-contrast, cellular resolution 3D images of an intact opaque organism.

Yet, despite the strengths of metal-stained CT imaging, a key remaining advantage of classical histology remains, i.e., the ability to use different color stains that target different cellular components, multiplying the specific biological information encoded in the images, and yielding differentiation of tissue types. The staining of biological tissues with two separate dyes, e.g., blue dye (hematoxylin) for nucleic acids and pink dye (eosin) for proteins, has allowed scientists to discern essentially every cell type. In optical histology, multi-color stains can also target cell membranes, nucleic acids, muscle fibers, and the like. Thus far, however, no one has developed a multiple stain process available for effective 3D phenotype imaging.

SUMMARY OF THE INVENTION

The present disclosure provides techniques for anato-morphological phenotyping of opaque organisms, such as zebrafish. 3D "color" X-ray histology systems have been developed that use multiple, heavy-metal stains and a multi-energy acquisition technique.

In some examples, multiple different monochromatic X-rays may be used to illuminate the sample from which emissions are collected and imaged through an optical conversion process. In such examples, a single layer scintillator may be used for conversion of incoming particles to optical energy that is detected by an imaging system. The X-ray sources in such examples may be synchrotrons, for example.

In other examples, such as for benchtop sized devices, an X-ray tube may be used as the X-ray source, one that unlike a synchrotron produces a wide spectrum of energies, termed a polychromatic spectrum of energies. In such examples, a conventional micro CT scanner may be used to acquire multiple sets of image data from the different illumination spectra (e.g., a high-energy image and a low-energy image).

Another example includes an X-ray tube that produces a single wide spectrum illumination with a single detector that is able to distinguish X-rays of different energies, such as photon counting detectors.

For any of the various techniques, a variety of biologically specific heavy-metal stains may be used for targeting various biologic targets. Example staining agents contain osmium or uranium, for example. With the present X-ray imaging systems, it is possible to differentiate the stains, because metals have X-ray absorption edges at different energies that are distinguishable using the suggested multi-energy acquisition strategy.

The techniques are described with reference to examples performed on model organisms, such as zebrafish. Yet, it will be appreciated that the techniques may be applied to any pathology sample that includes biologic targets, including, but not limited to lipids, cell membranes, general targets such as nucleic acids, fibrin, collagen, connective tissue, cell nuclei, proteins, DNA, and reticula. The samples may be ex vivo samples of tissue, for example, human, mammalian, or non-mammalian tissue removed from a host body, organ, or other tissue sample. While in other examples, the sample may be examined in vivo.

In accordance with an example, an apparatus for imaging biologic targets within a sample, the apparatus includes: an X-ray source configured to produce a micro-focused X-ray energy; the sample positioned to receive the micro-focused X-ray energy, the sample containing a plurality of biologic specific stains each staining a different biologic target within the sample; an X-ray responsive substrate configured to produce an output corresponding to the plurality of biologic specific stains within the sample; and an imaging stage configured to produce an image of each of the different stained biologic targets within the sample from the output of the X-ray responsive substrate.

In accordance with another example, a method of X-ray imaging and discriminating biologic targets within a sample, the method includes: staining the sample with a plurality of biologic specific stains each staining a different one of the biologic targets within the sample; dynamically illuminating the stained sample with micro-focused X-ray energy; collecting, into an X-ray responsive substrate, output X-ray energy from the illuminated sample, where that output X-ray energy from the illuminated sample is formed of different X-ray energy regions corresponding to the different biologic specific stains; and imaging each of the biologic targets based on output from the X-ray responsive substrate corresponding to the plurality of biologic specific stains within the sample.

DETAILED DESCRIPTION

Various examples are provided of 3D X-ray imaging techniques that use multiple heavy-metal stains of model organisms or other biologic targets and multiple captured datasets to produce stain-based images, where each dataset contains different X-ray energy information.

Generally, these techniques may be implemented using different types of X-ray illumination sources, including monochromatic X-ray energies, such as those generated by synchrotrons, and polychromatic (wide spectrum) X-ray energies, such as generated by X-ray tubes. Samples may be illuminated multiple times or a single time, depending on the type of X-ray energy and the type of X-ray detector. Numerous different examples are provided, and persons of ordinary skill will appreciate yet others in light of the following.

Figure 1:
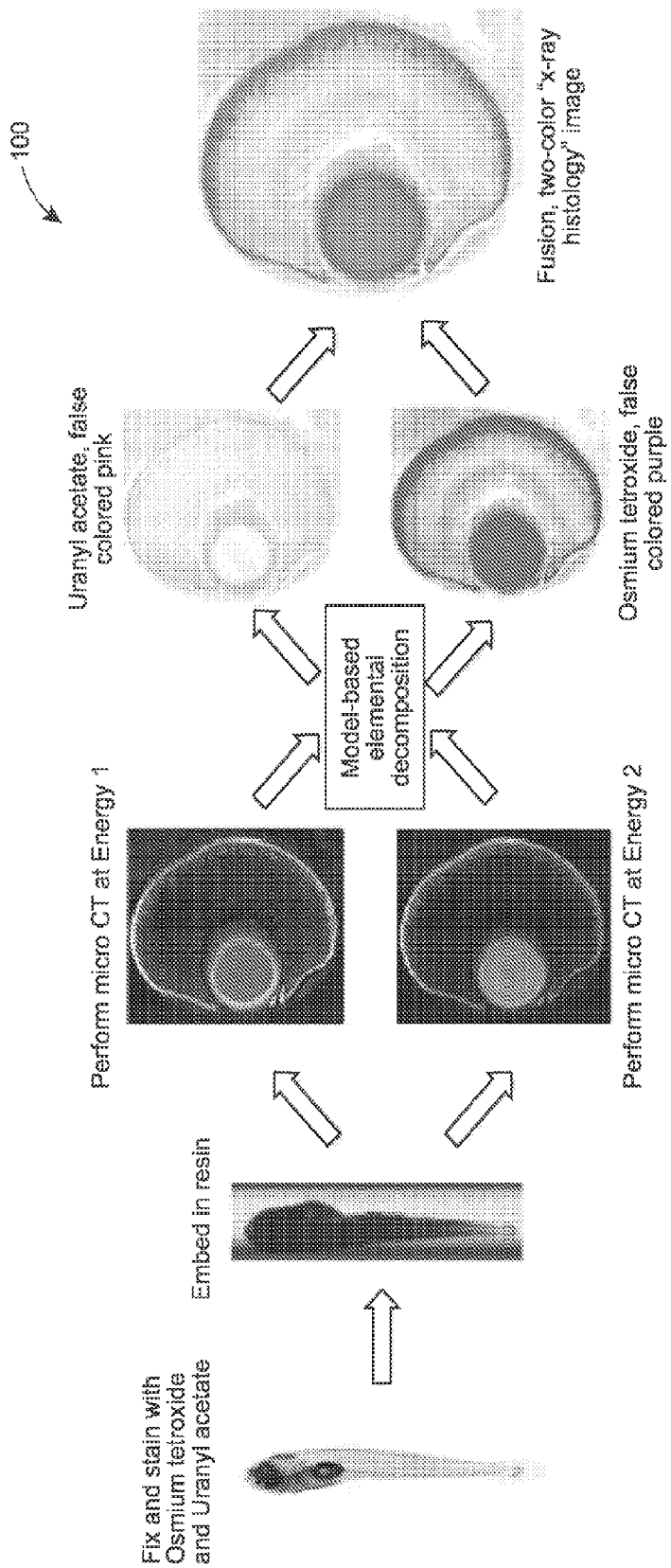
FIG. 1 illustrates an example process for x-ray imaging of multi-stained biologic target, in accordance with an example.

FIG. 1 provides process 100, in accordance with an example of the present techniques. In this example, the sample is a model organism, although the process (as with any process herein) may be used with any biologic target. Specifically, an intact zebrafish is fixed and stained with solutions of multiple, different heavy-metal staining agents. In the illustrated example, two staining agents are used, osmium tetroxide and uranyl acetate (each in 1% solutions). From here, the stained zebrafish are then embedded in resin and mounted on sample holders for synchrotron-based micro CT.

Micro CT images are acquired at two or more monochromatic X-ray energies (Energy 1 and Energy 2), from which a model-based elemental decomposition is performed to determine the distributions of two heavy-metal stains, described herein using the shorthand heavy-metals osmium (Os) and uranium (U), in the images, individually, resulting in the two images as shown. For this example, the model-based elemental decomposition may utilize the fact that osmium has an $L_3$ edge at 10.87 keV across which the photoelectric absorption cross section increases from 80.3 $cm^2/g$ to 207.8 $cm^2/g$ and that uranium has an $L_3$ edge at 17.17 keV across which the photoelectric absorption cross section increases from 43.3 $cm^2/g$ to 103.7 $cm^2/g$. In general the staining agents may be chosen, at least in part, because of their differing x-ray absorption and biological targeting properties.

With the two model-based elemental decomposition images formed, the process 100 may then include fusing these images together to form a multi-color X-ray histology image. In this example, the fused image is a two-color image, due to the use of two staining agents, osmium and uranium. However, in other examples, and as discussed below, three or more staining agents may be used allowing for high-color fused images.

While fixing and staining of zebrafish is provided in FIG. 1, it will be appreciated that any opaque organism suitable for phenotype analysis may be used. Examples include per category fish (e.g., paddlefish, zebrafish, axolotl, and pike), mammals (e.g. mouse embryos), insects (e.g., neuropteran, mantophasmid, flesh fly), and others (e.g., chick embryos, xenopus, squid).

In a particular implementation of the overall process 100, sample preparation and staining involved sacrificing three 5 dpf wild-type zebrafish, buffered in 1× PBS (phosphate buffered saline), and fixed in 10% NBF (neutral buffered formalin). One fish was stained with osmium tetroxide alone, one with uranyl acetate alone, and one with both. For the osmium tetroxide staining, the fixed fish was rinsed with 1× PBS, and then post-fixed with a 1% osmium tetroxide, 1× PBS solution for 24 hours. For the uranyl acetate staining, the fish was rinsed with 1× PBS, then again with 35% ETOH, and post-stained with 1% Uranyl acetate, and 50% EtOH for 24 hours. For the double-stained fish, the above staining procedures were applied sequentially. The zebrafish were then placed in a Kapton tube and embedded in a hard plastic resin. From here, the imaging and decomposition steps were performed.

The model-based elemental decomposition is designed to isolate from the CT images emissions and thus specific imaging data corresponding to the different stains used on the model organism. The decomposition procedure may vary depending upon the number of energy sources used to capture the micro CT or other images of the zebrafish.

In an implementation, the elemental decomposition was performed assuming the fixed zebrafish specimen contained three known materials present in unknown, spatially varying concentrations: osmium, uranium, and a background material. The background material was assumed to have the same energy-dependent X-ray attenuation properties as water, which is a good approximation for most biological/organic material. The reconstructed CT images at each energy yielded the total linear attenuation coefficient in the specimen on a voxel-by-voxel basis.

The model for the reconstructed linear attenuation coefficient, measured in $cm^{-1}$, of a given voxel i at energy $E_j$ is expressed by $$\mu_i(E_j) = \alpha_j^{Os}\rho_i^{Os} + \alpha_j^{U}\rho_i^{U} + \alpha_j^{BG}\rho_i^{BG}, \quad (Eq.\ 1)$$

where the term $\rho_i^X$ denote the densities of material X(Os, U, or BG-background) at voxel i in g/cm³ and the coefficients $$\alpha_j^X \overset{def}{=} \left[\frac{\mu}{\rho}(E_j)\right]_X$$

denote the mass-attenuation coefficients of materials X at energy $E^j$, in cm²/g. These mass-attenuation coefficients are well characterized and may be obtained from the National Institute of Standards and Technology (NIST) XCOM database. Eq. 1 represents a linear combination of the three unknown material densities in voxel i. Imaging with energy information provides multiple different linear combinations of the stains and the resulting system of linear equations can be solved for the unknown stain images. This model of elemental decomposition may be applied across any different energy decomposition strategy. For example, if images are acquired at three different beam energies, i.e., at a triple-energy decomposition strategy, Eq. 1 becomes a system of three equations in the three unknown densities at each voxel. The coefficients of the equations are the same at all voxels and thus the resulting solution is equivalent to taking appropriate linear combinations of the three images to obtain the images of the osmium, uranium, and background distributions. Specifically, the three energy measurements yield the following equations:

$$\mu_i(E_1) = \alpha_1^{Os}\rho_i^{Os} + \alpha_1^{U}\rho_i^{U} + \alpha_1^{BG}\rho_i^{BG}$$

$$\mu_i(E_2) = \alpha_2^{Os}\rho_i^{Os} + \alpha_2^{U}\rho_i^{U} + \alpha_2^{BG}\rho_i^{BG}$$

$$\mu_i(E_3) = \alpha_3^{Os}\rho_i^{Os} + \alpha_3^{U}\rho_i^{U} + \alpha_3^{BG}\rho_i^{BG}, \quad (Eq.\ 2)$$

This can be written as a matrix equation $$\vec{\mu}_i = A\vec{\rho}_i, \quad (Eq.\ 3)$$

where $\vec{\mu}_i = [\mu_i(E_1), \mu_i(E_2), \mu_i(E_3)]$, $\vec{\rho}_i = [\rho_i^{Os}, \rho_i^{U}, \rho_i^{BG}]$, and $$A = \begin{pmatrix} a_1^{Os} & a_1^{U} & a_1^{BG} \\ a_2^{Os} & a_2^{U} & a_2^{BG} \\ a_3^{Os} & a_3^{U} & a_3^{BG} \end{pmatrix}. \quad (Eq.\ 4)$$

The solution is given by $$\vec{\hat{\rho}}_i = A^{-1}\vec{\mu}_i, \quad (Eq.\ 5)$$

where $A^{-1}$ denotes the inverse of the matrix A, which exists so long as the determinant of A is non-zero. The caret notation $\hat{\rho}$ indicates that this represents an estimate of $\vec{\rho}_i$, which may differ from the true value due to noise or bias. The matrices A and $A^{-1}$ are independent of the pixel index i, so the process for obtaining the three different component images, $\hat{\rho}_i^{Os}, \hat{\rho}_i^{U}, \hat{\rho}_i^{BG}$, for all pixels i is simply to take linear combinations of the multi-energy attenuation images $\mu_i(E_1)$, $\mu_i(E_2)$, $\mu_i(E_3)$ as dictated by the components of the matrix $A^{-1}$.

If on the other hand, images are acquired at two different beam energies, i.e., at a dual-energy decomposition strategy, because the two stains are typically present in large concentrations and are strongly absorbing of X-rays, it may be possible simply to ignore the presence of the background material and perform a dual-energy, dual-material decomposition without incurring a large error. This would simplify the acquisition process and could reduce the noise in the decomposed images, albeit at the cost of bias. As shown below, this bias may be minimized through judicious choice of the two X-ray energies.

For example, if only the two stain materials are present, the following model would arise $$\mu_i(E_1) = \alpha_1^{Os}\rho_i^{Os} + \alpha_1^{U}\rho_i^{U}$$

$$\mu_i(E_2) = \alpha_2^{Os}\rho_i^{Os} + \alpha_2^{U}\rho_i^{U}, \quad (Eq.\ 6)$$

The estimates of the two unknown densities would be obtained by inverting the resulting 2×2 matrix of coefficients, yielding the following compact solution $$\hat{\rho}_i^{Os} = \frac{a_2^{U}}{D}\mu_i(E_1) - \frac{a_1^{U}}{D}\mu_i(E_2) \quad (Eq.\ 7)$$

$$\hat{\rho}_i^{U} = -\frac{a_2^{Os}}{D}\mu_i(E_1) + \frac{a_1^{Os}}{D}\mu_i(E_2),$$

where $$D = \alpha_2^{U}\alpha_1^{Os} - \alpha_1^{U}\alpha_2^{Os} \quad (Eq.\ 8)$$

is the determinant of the system of equations.

The presence of a third, background, material means that the two stain measurements are actually given by $$\mu_i(E_1) = \alpha_1^{Os}\rho_i^{Os} + \alpha_1^{U}\rho_i^{U} + \alpha_1^{BG}\rho_i^{BG} \quad (Eq.\ 9)$$

and $$\mu_i(E_2) = \alpha_2^{Os}\rho_i^{Os} + \alpha_2^{U}\rho_i^{U} + \alpha_2^{BG}\rho_i^{BG} \quad (Eq.\ 10)$$

Plugging these into Eq. 7 yields $$\hat{\rho}_i^{Os} = \rho_i^{Os} + \left[\frac{a_1^{BG} a_2^U - a_1^U a_2^{BG}}{D}\right]\rho_i^{BG} \quad \text{(Eq. 11)}$$

and $$\hat{\rho}_i^{U} = \rho_i^{U} + \left[\frac{-a_1^{BG} a_2^{Os} + a_1^{OsU} a_2^{BG}}{D}\right]\rho_i^{BG}. \quad \text{(Eq. 12)}$$

The second term in each expression is the error term arising due to the presence of the background material that we've neglected in this dual-energy decomposition strategy. The pair of energies used for the decomposition can be chosen to minimize the coefficients in square brackets, which depend only on the mass attenuation coefficients of the materials present and not on their concentrations in the sample.

To demonstrate the feasibility of the multi-stain, multi-energy technique, synchrotron micro CT imaging was first performed at four widely spaced energies distributed below, above, and between the absorption edges of osmium and uranium. In order to validate the decompositions obtained by use of the proposed approach, a second set of synchrotron micro CT images were obtained of the same samples with very narrowband radiation tightly bracketing the absorption edges, allowing for L-edge subtraction.

For the initial micro CT imaging set, the synchrotron micro CT imaging was first performed at beamline 2-BM-B of the Advanced Photon Source (APS) at Argonne National Laboratory, in Illinois. The specimens were mounted on a sample holder magnetically secured to a rotation stage. The beam was monochromatized using a multilayer monochromator with bandwidth $\Delta E/E \sim 1.5\%$. This monochromator was precalibrated at a discrete set of energies. The four energies used were 9.3, 13.8, 18.5, and 22.5 keV. Exposure times can be made to vary per energy to achieve approximately comparable levels of transmission at the various beam energies. In this example, exposure times of 600 ms (at 9.3 keV), 400 ms (at 13.8 keV), 200 ms (at 18.5 keV), and 150 ms (at 22.5 keV) per frame were used. A 5-layer diffuser was used to smooth structure in the illumination field, which helped suppress ring artifacts in the reconstructed images. The sample-to-detector distance may be adjusted, but for this example was set to 30 mm to provide slight phase-contrast induced edge enhancement without distracting overshoots. The transmitted X-rays were converted to optical photon emissions by a 250-micron thick scintillator made of LuAG:Ce. The optical emissions were focused through a 10× lens (Mitutoyo Inc) onto a Peltier-cool CCD (Coolsnap HQ, Photometrics, Inc.), and 1500 projection images were acquired over an 180 degree scan area.

Image reconstruction was performed using the Gridrec algorithm (J. D. O'Sullivan, "A Fast Sinc Function Gridding Algorithm for Fourier Inversion in Computed Tomography", IEEE Trans on Medical Imaging, vol. MI-4, no. 4, pp 200-207, December, 1985) onto a grid of voxels, e.g., 743 nm voxels in this example. Residual ring artifacts were suppressed by an algorithm that segments and subtracts circular and partially circular features centered precisely on the axis of rotation.

The second micro CT imaging set of the dual-stained zebrafish was performed at beamline 13-BM-D, at Argonne National Laboratory, equipped with a double-layer silicon crystal monochromator. This monochromator has a much narrower bandwidth ($\Delta E/E \sim 0.01\%$), which allows tight bracketing of the L3 edges of the stains, albeit at commensurately reduced photon flux. Images were acquired at energies 10.82 and 10.92 keV to bracket the osmium edge and 17.12 and 17.22 keV to bracket the uranium edge.

The sample-to-detector distance was again set to 30 mm and 1200 projection images were acquired over 180 degrees. For the uranium-edge imaging, acquisition time per frame was set to 3 s and for the osmium edge to 9 s (to compensate for lower penetration at the lower energy). The total imaging time for each pair of energies was much longer than that of the first set of images (approximately 2 hours for uranium and 6 hours for osmium) compared to between 10 and 20 minutes for the first set of images. The total imaging time of course can be variable set, for example, to compensate for differences in flux obtained from different monochromators or other conditions. Generally speaking, even with longer imaging times, approximately 10 times fewer X-rays may contribute to each measurement, so noisier images are expected from the L-edge subtraction.

In this example, the transmitted X-rays were converted to optical photons by a 100-micron thick scintillator made of LuAG:Ce. The optical emissions were focused through a 10× lens (Mitutoyo Inc) onto a Peltier-cool CCD (Coolsnap HQ, Photometrics, Inc.). In this example, we imaged above and below both edges in the double stained fish; and image reconstruction was again performed using the Gridrec algorithm.

These examples describe performing multiple illuminations of monochromatic X-rays on the sample and converting the resulting data to optical photons using a single material, single layer scintillator, i.e., a non-spectral specific detector.

Figure 2:
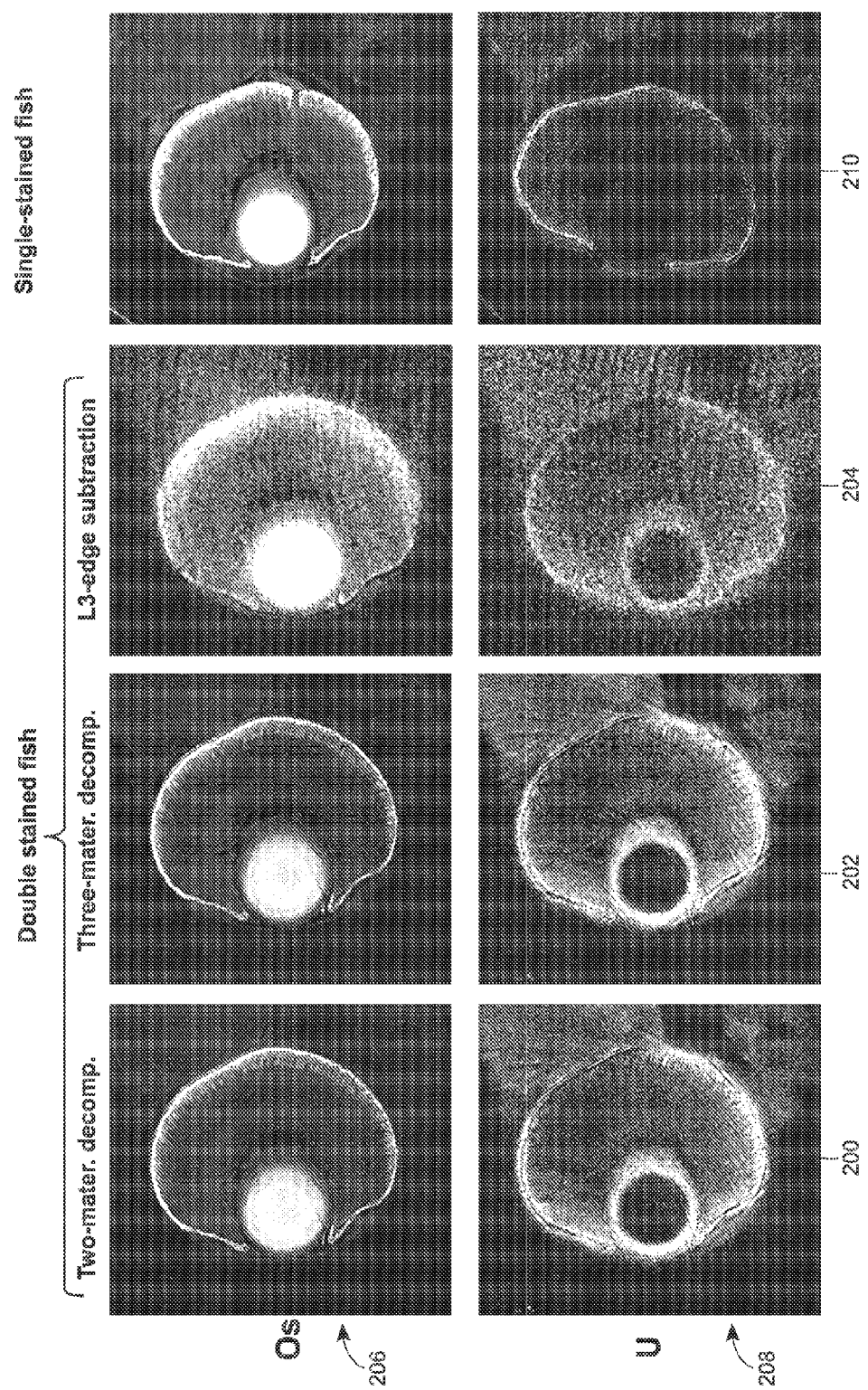
FIG. 2 illustrates images of a multi-stained biologic target, comparing different multi-energy decompositions techniques, in accordance with some examples.

FIG. 2 illustrates an example comparison of multi-energy decompositions. The three left columns 200, 202, and 204 show the osmium distributions (row 206) and uranium distributions (row 208) for a double-stained fish as estimated using three different approaches: dual-energy imaging using energies 13.8 and 18.5 keV (column 200), triple-energy imaging using energies 9.3, 13.8, and 18.5 keV (column 202), and gold-standard (albeit noisy) L-edge subtraction (column 204). The comparison demonstrates that the elemental decomposition approach is robust, with all three methods producing qualitatively similar results. The right-most column 210 shows the osmium and uranium estimates for two different zebrafish, each stained with one metal or the other. While these images are not expected to match exactly those in columns 200-204, since they come from different zebrafish, they show that the stains have similar distributions when applied singly as when applied jointly.

Thus, the presence of the osmium stain does not prevent the uranium stain from reaching the targets it reaches when it is used alone, demonstrating that the two stains do not interfere with each other.

To explore the accuracy and robustness of the dual-energy decomposition method, the mean value of osmium and uranium concentration in two different regions of the image was calculated and analyzed over an osmium-rich region (the lens of the eye) and a uranium-rich region (the brain). First, the concentrations values were calculated from the L-edge subtraction images. Next, these L-edge subtraction values, which should be unbiased, were taken as the gold standard to which the values obtained by dual-energy decomposition could be compared in order to obtain a "measured percent bias." Finally, the error expressions from Eqs. 11 and 12 were examined assuming a background concentration of 1000 mg/cm$^3$ of water in order to obtain the "expected % bias." The results are given in Table 1 below for the osmium-rich region and Table 2 for the uranium-rich region.

For the concentration of osmium in the osmium-rich region, the agreement between the measured and expected percent bias figures was generally excellent; all the percent biases were relatively low because the concentration of osmium is so high in the region. For the concentration of uranium in the osmium-rich region, which is lower by an order of magnitude, it can be seen that the (9.3, 13.8 keV) and (9.3, 18.5 keV) pairs are poor choices, in this example, yielding expected and measured percent biases in excess of 200%. The three remaining pairs should, in principle, have percent biases below 10% at this concentration, but the measured percent biases are somewhat higher, especially for the pairs involving the image acquired at 22.5 keV. This table suggests that the 13.8, 18.5 keV pair would be a good choice for further analysis.

TABLE 1

L-edge and dual-energy results for an osmium-rich region of interest (values are in mg/cm$^3$)

| Energies (keV) | Osmium meas. mean | Osmium meas. % bias | Osmium expected % bias | Uranium meas. mean | Uranium measured % bias | Uranium expected % bias |
|---|---|---|---|---|---|---|
| L-edge | 242.7 | N/A | N/A | 11.3 | N/A | N/A |
| 9.3, 13.8 | 250.4 | 3.2% | −1.2% | 33.6 | 198.0% | 292.9% |
| 9.3, 18.5 | 215.6 | −11.2% | −20.6% | 54.0 | 379.2% | 541.3% |
| 13.8, 18.5 | 261.2 | 7.6% | 4.7% | 9.2 | −18.5% | −7.8% |
| 13.8, 22.5 | 262.7 | 8.2% | 4.5% | 5.8 | −48.6% | −0.9% |
| 18.5, 22.5 | 267.8 | 10.3% | 3.9% | 2.7 | −76.5% | 8.9% |

Similar results are seen in the uranium-rich region of Table 2. The amount of osmium is lower by an order of magnitude, so the percent biases for osmium are much higher because the absolute biases are independent of the amount of osmium. The agreement with the predicted biases is also not as close due to statistical fluctuations. The uranium, now present in four-times greater concentration than in the lens of the eye, shows very good agreement of measured bias with expected bias. The results again indicate that the pairs involving the 9.3 keV energy images are poor choices, in this example. The pairs involving the 22.5 keV image have lower bias for uranium than in the osmium-rich region, but the measured bias for osmium is high. On this basis, the 13.8, 18.5 keV pair was used for further analysis, in this example.

TABLE 2

L-edge and dual-energy results for a uranium-rich region of interest (values are in mg/cm$^3$)

| Energies (keV) | Osmium meas. mean | Osmium meas. % bias | Osmium expected % bias | Uranium meas. mean | Uranium measured % bias | Uranium expected % bias |
|---|---|---|---|---|---|---|
| L-edge | 28.6 | N/A | N/A | 43.5 | N/A | N/A |
| 9.3, 13.8 | 43.1 | 50.5% | −9.7% | 61.4 | 41.0% | 73.2% |
| 9.3, 18.5 | 33.6 | 17.4% | −171.7% | 74.9 | 72.0% | 135.3% |
| 13.8, 18.5 | 49.3 | 72.3% | 38.8% | 47.2 | 8.4% | −1.9% |
| 13.8, 22.5 | 50.4 | 76.1% | 37.4% | 44.6 | 2.4% | 0.2% |
| 18.5, 22.5 | 56.6 | 97.6% | 32.4% | 43.8 | 0.5% | 2.2% |

The quantitative results obtained for the triple-energy decomposition method are given in Tables 3 and 4 for the osmium- and uranium-rich regions, respectively. Expected and measured biases were not listed since the technique is, in principle, unbiased depending on if the model assumptions are correct. The Tables 3 and 4 do include, in addition to the mean concentration in the regions of interest (ROI), the standard deviation of the ROI voxel values. This standard deviation value should not be interpreted as the precision of the elemental decomposition approach, since in addition to such random effects it includes a significant contribution from the non-uniform distribution of the stain with the region. It can, however, be used to compare the precision of the decomposition obtained with the various triplets of energies since differences in ROI noise would reflect differences in the conditioning of the inverse problem.

It can be seen that all three triplets produce very similar results for mean osmium value, with excellent agreement with gold standard L-edge subtraction in the osmium-rich region, and a large overestimate of osmium concentration in the uranium-rich region. The 9.3, 13.8, and 18.5 keV triplet yields the most accurate estimate of uranium concentration in the osmium-rich region. All three triplets produce comparable values of uranium in the uranium-rich region. The true concentration of the background material is not known, though it is expected to be on the order of 1000 mg/cm$^3$. The decomposition yields values of that order of magnitude and it is encouraging that the accuracy of the osmium and uranium estimates seem robust to variations in the estimate of the background.

It can be seen that the 9.3, 18.5, and 22.5 keV triplet has a significantly higher ROI standard deviation than the other two triplets. This is because the determinant of the 3×3 matrix being inverted in that case is only 14,062, vs. 57,448 for 9.3, 18.5, and 22.5 keV and 47,221 for 9.3, 18.5, and 22.5 keV. Based on these results, either of the latter triplets are good choices; and the 9.3, 13.8, and 18.5 keV triplet was used for further analysis.

TABLE 3

L-edge and triple-energy results for an osmium-rich region of interest

| Energies (keV) | Osmium ROI Mean | Osmium ROI Std. Dev. | Uranium ROI Mean | Uranium ROI Std. Dev. | Water ROI Mean | Water ROI Std. Dev. |
|---|---|---|---|---|---|---|
| L-edge | 242.7 | 16.7 | 11.3 | 20.5 | N/A | N/A |
| 9.3, 13.8, 22.5 | 252.8 | 10.1 | 5.4 | 14.0 | 867.5 | 523.4 |
| 9.3, 13.8, 18.5 | 252.5 | 10.5 | 9.5 | 19.3 | 741.9 | 625.0 |
| 9.3, 18.5, 22.5 | 259.0 | 34.3 | 1.6 | 30.8 | 873.9 | 541.5 |

TABLE 4

L-edge and triple-energy results for a uranium-rich region of interest

| Energies | Osmium ROI Mean | Osmium ROI Std. Dev. | Uranium ROI Mean | Uranium ROI Std. Dev. | Water ROI Mean | Water ROI Std. Dev. |
|---|---|---|---|---|---|---|
| L-edge | 28.6 | 14.6 | 43.5 | 17.6 | N/A | N/A |
| 9.3, 13.8, 22.5 | 44.5 | 14.4 | 44.3 | 14.8 | 520.3 | 776.2 |
| 9.3, 13.8, 18.5 | 44.3 | 14.3 | 47.3 | 21.0 | 430.5 | 948.9 |
| 9.3, 18.5, 22.5 | 48.9 | 42.0 | 41.6 | 33.8 | 524.9 | 786.5 |

Figure 3:
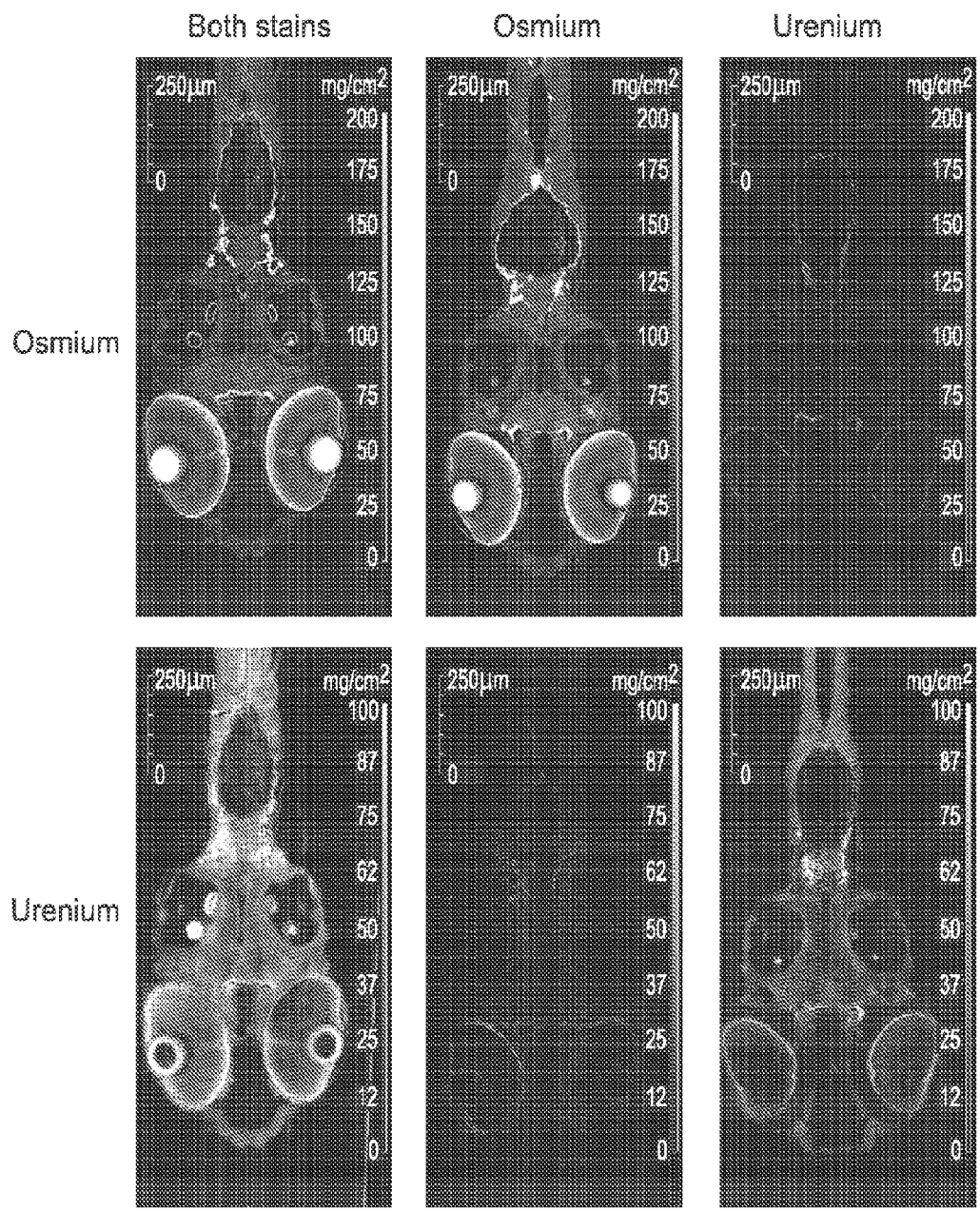
FIG. 3 illustrates sagittal osmium and uranium decomposition images obtained from the dual- and single-stained zebrafish.

FIG. 3 illustrates a set of sagittal osmium and uranium decomposition images obtained from the dual- and single-stained zebrafish, respectively. An effort was made to choose anatomically aligned slices from these three different samples. As shown, there is very little signal in the uranium image obtained from the osmium-only fish or in the osmium image obtained from the uranium-only fish. The distribution of osmium calculated in the dual- and osmium-stained fish are qualitatively very similar, albeit with slightly more variability in the dual-stained fish image, likely due to slight contamination from uranium signal. The two uranium images are somewhat more dissimilar, likely due to contamination from the stronger osmium signal. This suggested that the use of stain pairs that achieve approximately similar levels of staining, with different spatial distributions, may be preferable.

In the example of FIG. 1, the multi-energy CT decomposition step yielded two separate image volumes for the two different stains. These images can be analyzed independently, while in other examples these images may be fused together for a single presentation that allows visualization of stain co-localization and complementarity. Unlike traditional optical histology, where the image is naturally fused with a predetermined color scheme, this virtual histology allows images to be combined with arbitrary color schemes and degrees of blending.

Figure 4:
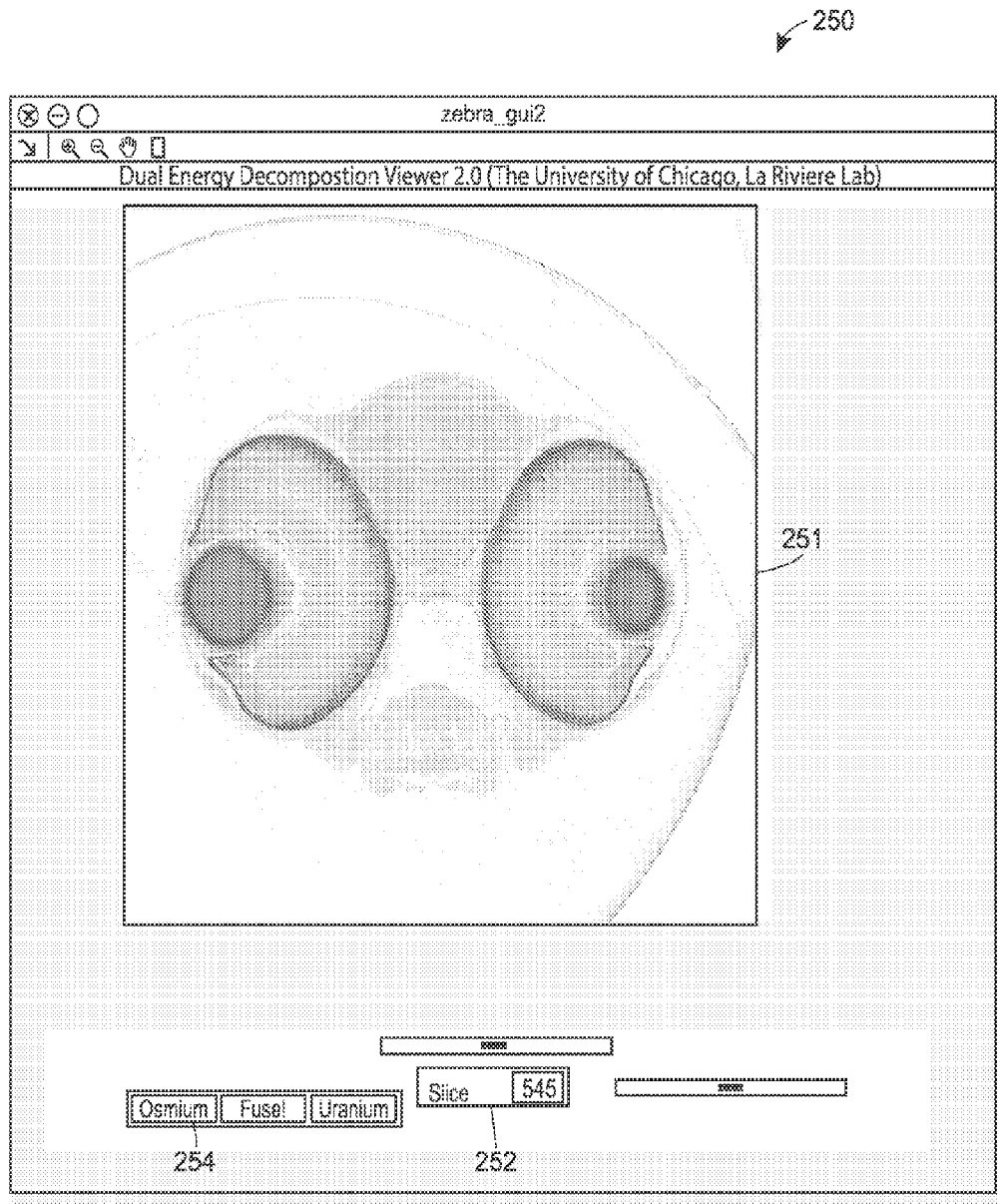
FIG. 4 is a screenshot of a stain-based image depicted by a viewer module running on an image processing computer.

The present techniques are able to produce a virtual histology image fusion viewer having a screenshot 250 shown in FIG. 4. The viewer, which may run a imaging processing computer, depicts the screenshot 250 on a monitor, where the screenshot 250 is of a slice 251 (termed slice 545) of a zebrafish. The slice number may be selected by a user from among the captured image data, through a slice selector input box 252. The screenshot 250 is a stain-based image, where the particular stain displayed (e.g., Osmium, Uranium, or a fused combination of the two) is selectable by the user, through an input box 254.

Figure 5:
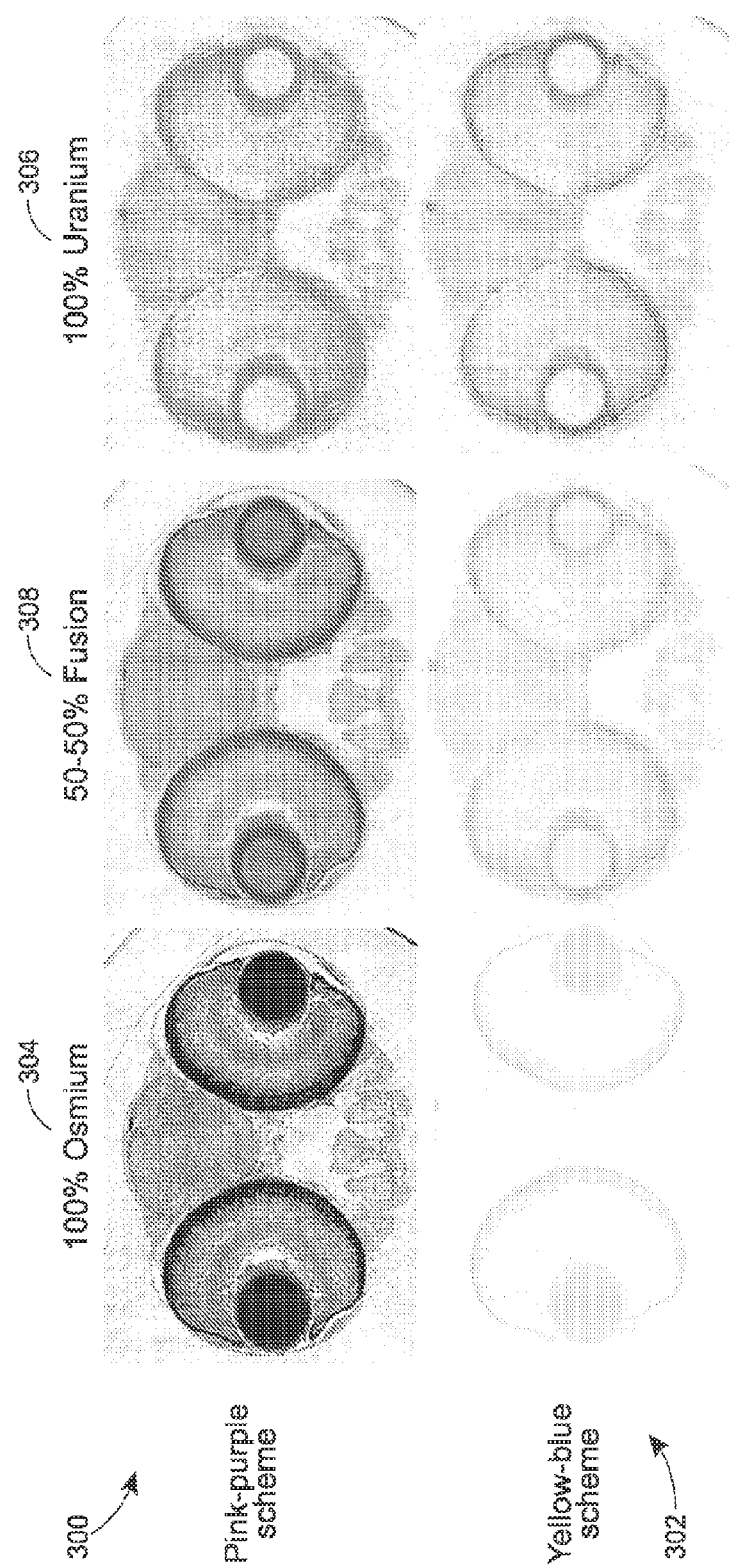
FIG. 5 illustrates two sets of potential imaging schemes of different stain images as may be implemented by the viewer module of FIG. 4.

FIG. 5 illustrates two potential color schemes. A first color scheme 300, called the pink-purple scheme, was chosen to create images with an appearance similar to H&E-stained pathology images. A second color scheme 302, called the yellow-blue scheme, was chosen as an example of the use of true complementary colors that allow for clearer visualization of the regions that are predominantly stained with one metal or the other. For the 100% Os stain, column 304, the first color scheme using a purely purple color scheme, while the 100% Ur stain, column 306, uses a purely pink color scheme, and the combined 50%-50% fused image, column 308, is formed of both color schemes providing the advantage of allowing both elements to be viewed simultaneously in a color scheme reminiscent of traditional histology. Similarly, for the second color scheme, the 100% Os stain case is a purely yellow color scheme, the 100% Ur stain case is a purely blue color scheme, and the 50%-50% fused image is a combination of the two.

Figure 6:
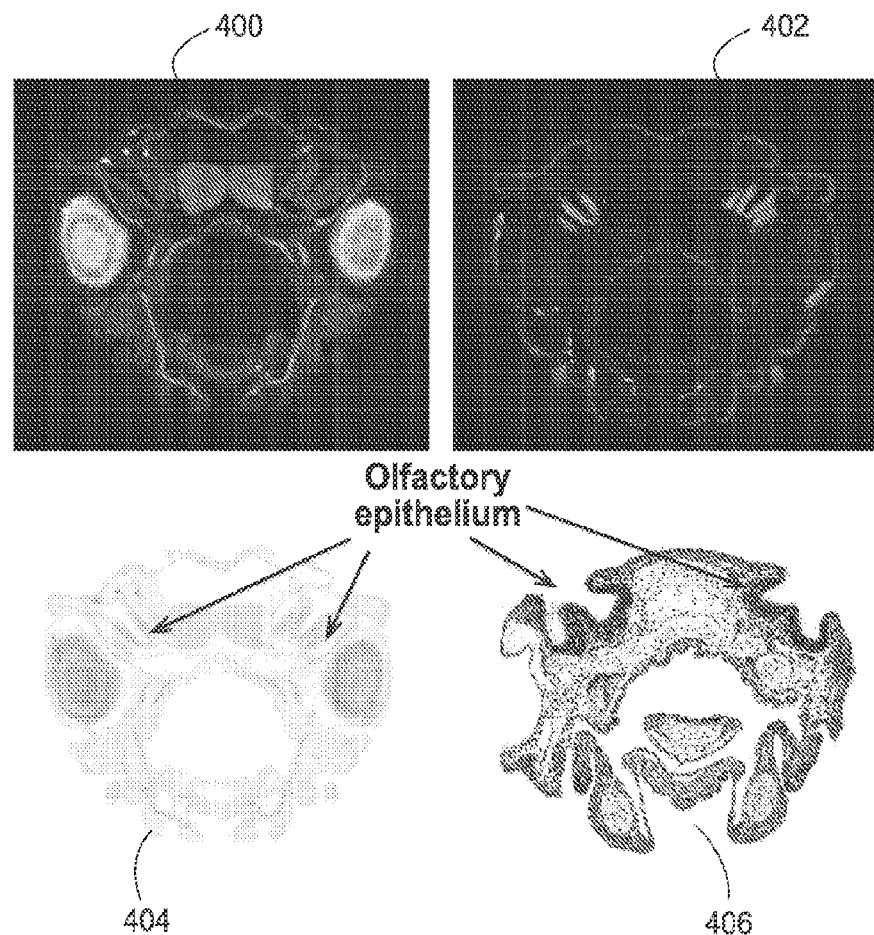
FIG. 6 illustrates the decomposition from captured computed tomography images into different stain channels, in accordance with an example.

In addition to the foregoing, staining and imaging of a juvenile (33 dpf) wild-type zebrafish was also performed using the same protocol described for the larval fish. The X-ray energies employed were 16.6 and 17.4 keV, bracketing the uranium L edge. The higher energies gave better results in this larger fish because they allowed greater penetration of the larger fish. FIG. 6, for example, shows the decomposition from captured micro CT images 400 and 402 into osmium and uranium channels, as well as virtual histology image created by a 25%-75% osmium-uranium blend using a red-green color table, image 404. Also shown is an H&E stained histology slice 406 from an aged matched fish. It can be seen that the uranium distribution correlates well with the haematoxylin (purple) stain (images 402 and 406), especially in the olfactory epithelium and other distal structures in the slice.

Thus, as described above, the present techniques have been used to stain an intact, three-dimensional organism with two heavy-metal stains and determine the spatial distribution of those stains at high cellular resolution using multi-energy micro CT. With the resulting image data, the techniques may be used for phenotyping of millimeter scale model organisms, such as the zebrafish shown here or others. The techniques can also be used to image millimeter scale or larger tissue specimens, allowing for isotropic 3D examination of pathology specimens, for example.

The use of both triple- and dual-energy decomposition strategies have been provided by way of example. We've demonstrated that multi-energy strategies can provide high-quality results if the imaging energies are chosen so as to minimize the bias that arises from implicitly ignoring the presence of a third, background material. In other examples, additional optimizations may be used to guide the choice of energy levels used, by for example considering both the bias and variance of the estimates, under the assumption that the data noise is dominated by Poisson counting statistics that worsen when fewer photons penetrate the object.

Some of the examples above demonstrate systems that use multiple illuminations of monochromatic X-ray energies. But these are provided by way of example. Thus, while experiments were conducted using a synchrotron capable of producing monochromatic X-ray energies, in other examples polychromatic X-ray energy may be used, for example, when using a benchtop system and an X-ray tube radiation source. In such systems, the illuminating X-ray energy can be achieved either by varying the illumination spectrum from an X-ray tube or by using energy-sensitive detectors (such as a photon-counting detector). The resulting data may no longer yield a simple pair of linear equations, as when performing monochromatic acquisitions, but rather a pair of non-linear equations that can still be solved quantitatively in the data domain for the projections of the two stains of interest. Image acquisition times, however, might be longer in some benchtop systems, to achieve similar image quality. But the flexibility of use that results from these small systems would be advantageous for many applications.

Figure 7:
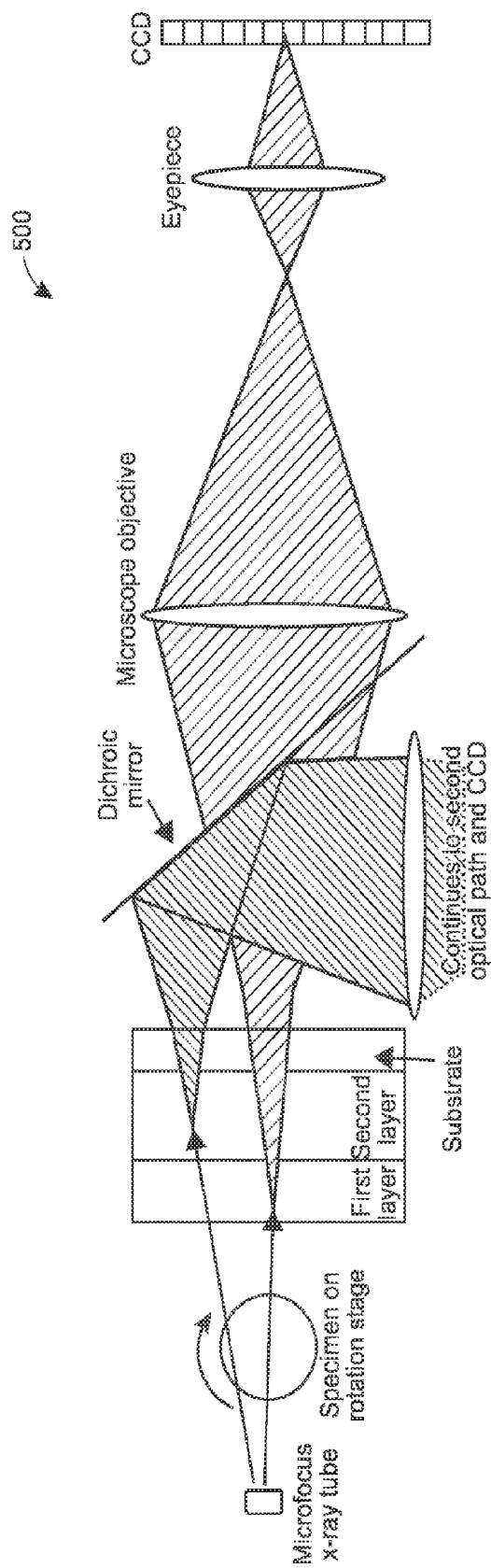
FIG. 7 illustrates a schematic of a multi-layer, multi-color scintillator-based imaging system implementing the processes described herein and using an X-ray tube source, in accordance with an example.

FIG. 7 illustrates a schematic of a multi-layer, multi-color scintillator-based imaging system implementing the processes described herein and using an X-ray tube source. Conventionally, because of the lack of X-ray detectors with sufficiently small pixels, all micron-scale CT imaging is performed using single-layer scintillators coupled to optical CCDs through microscope objectives. The present techniques, in contrast, use a multi-layer, multi-color scintillator configuration 500. The configuration 500 provides registration of the various line integral measurements, and also greatly increases the overall detection efficiency, thus improving throughput. Furthermore, in conventional single-layer scintillators, the thickness of the scintillator must be matched to the depth of focus of the microscope objective, such that making the scintillator thicker leads to rapid degradation of resolution. The multi-layer multi-color scintillator avoids this sensitivity-resolution tradeoff by allowing different lens-CCD combinations to focus separately on the different layers, with layer discrimination based on light color.

Figure 8:
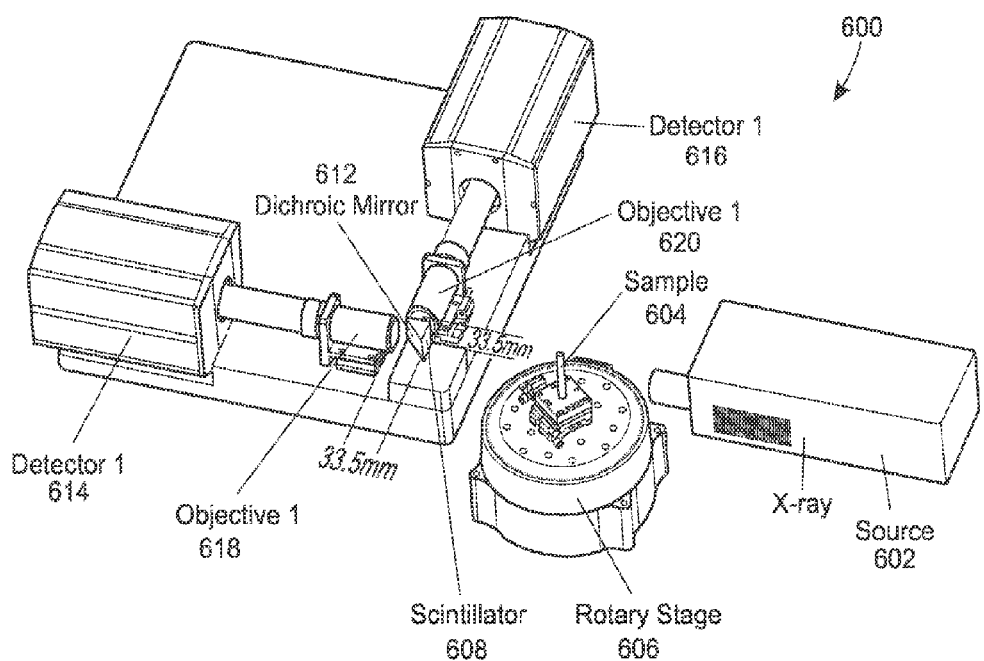
FIG. 8 illustrates an example implementation of the schematic of FIG. 7.

An example benchtop device implementation of the schematic 500 is shown in FIG. 8. A 3D X-ray color imaging system 600 includes an X-ray source 602, which may be internal or external to the system 600, and is to produce an output directed at a sample 604 mounted to a rotary stage 606. A scintillator 608 is mounted, in the illustrated example, to a separate support stage 610, along with a dichroic mirror 612 splitting sample emissions into one of two detectors 614, 616, each coupled through object lens 618, 620, respectively.

The X-ray source 602 may include a microfocus X-ray tube that illuminates the sample 604, which is mounted vertically on the rotation stage 606. The transmitted X-rays from the sample are converted into visible light of two different colors in the two layers of the multi-color scintillator 608. In the illustrated example, the colored light from the first layer passes through the dichroic mirror 612 at the back of the scintillator mount and is magnified by the objective lens 618 before impending upon a monochrome CCD as the detector 614. The differently colored light from the second layer is reflected by the mirror 612 into a second, identical optical subsystem having the object lens 620 and detector 616. Each optical system is focused on the appropriate layer of the scintillator.

The geometrical magnification of the system 600 may be represented as $M=(L_s+L_d)/L_s$, where $L_s$ is the source-to-sample distance and $L_d$ is the sample-to-detector distance. The resolution of this system may be presented as $$\delta = \sqrt{\left(\frac{M-1}{M}s\right)^2 + \left(\frac{\delta_{det}}{M}\right)^2},$$

where s is the size of the X-ray source spot, and $\delta_{det}$ is the detector resolution.

Some micro CT systems have relatively poor detector resolution and achieve high spatial resolution through geometric magnification with $L_d \gg L_s$, so that $M \gg 1$, and $\delta \approx s$. In a configuration where the sample is placed very close to the X-ray source, the resolution is roughly equal to the X-ray source size. In a configuration where the sample is placed close to the detector, the system resolution is primarily determined by the detector resolution. In an example implementation of this later configuration, the following geometry was used, M=1.5, and $\delta_{det}$=2 μm (nominal) so that δ=2.1 μm. The pixel size was set at 1 μm to meet the Nyquist sampling rate requirement. With a 4 million pixel CCD camera as the detectors, the field of view would be around 2 mm×2 mm. These values are provided for example purposes, of course.

The scintillator can be fabricated by different techniques. For example, one may fabricate the multi-color scintillator formed of a monolithic crystal of a single material grown with a change in the dopant material partway through the process, thereby creating the different layers. Since different dopants produce different colors of scintillation light, the desired multilayer, multi-color effect would result.

In another example, a multilayer scintillator can be assembled by attaching pairs of "commodity" scintillators, such as those produced by Crytur, Inc. of the Czech Republic, using adhesives, for example, epoxy. This approach allows for the use of different scintillation materials in the different layers. The approach also allows for assembling different pairs of scintillator materials for use in the testbed, since a small number of base materials can be used to make many combinations. Example scintillator layer materials include yttrium aluminium garnet (YAG), lutetium yttrium silicon oxide (LYSO), and lutetium aluminium garnet (LuAg).

Since the emission from the scintillator is omni-directional, an objective-coupled detection system equivalent to a microscope with incoherent illumination—similar to a fluorescence microscope, may be used. The resolution is expressed as $\delta_{\delta_\epsilon\tau}=0.61*\lambda/NA$. Therefore, the resolution of the detector's optical system is primarily determined by the scintillator emission wavelength and numerical aperture.

Preferably, the scintillator layer thicknesses should not exceed the depth of focus of the objective lens or the target resolution will not be achieved. In the illustrated example, the results indicate that achieving 2 micron resolution with a 0.28 NA lens meant keeping the thickness of each scintillator below 100 microns. Chromatic aberration was not a concern because each detection path operated on a single narrowly-peaked emission color. The scintillator substrate and dichroic mirror can introduce a modest amount of spherical aberration, but at a relatively low NA, the effect on resolution would be limited.

In an example implementation of the benchtop system of FIG. 8, we used a scintillator formed of two scintillator layers: one comprising 50 microns of YAG:Ce and the other comprising 100 microns of LuAG:Eu, with the YAG layer emitting primarily at 520 nm (green) and the LuAG layer emitting primarily at 600 nm (red). We then imaged a series of kapton tubes containing 1%, 2%, and 4% solutions of Iodine and Tungsten. We used a 10×, 0.28NA objective and a color CCD. The red and green channels of the CCD should then correspond to the images of the two different detector layers. Since a full scale calibration allowing decomposition in the data domain (as proposed in C.3.3 below) would have been time-prohibitive during our beamtime, we simply reconstructed CT images from the data acquired in each layer, one representing a "low-energy" image and the other a "high-energy" image in dual-energy CT nomenclature.

Figure 9:
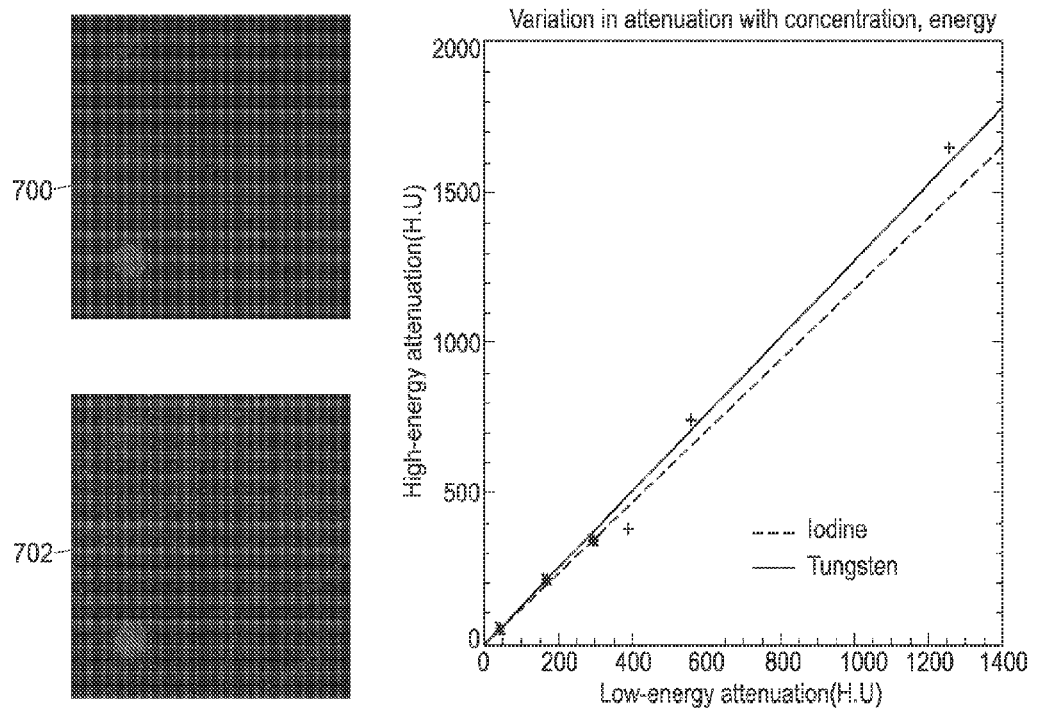
FIG. 9 is a plot of attenuation for a "low-energy" image and a "high-energy" image, in accordance with an example.

The results are shown in FIG. 9 in images 700 and 702, respectively, where image 700 is obtained from a front layer and image 702 is obtained from a rear layer.

Figure 10:
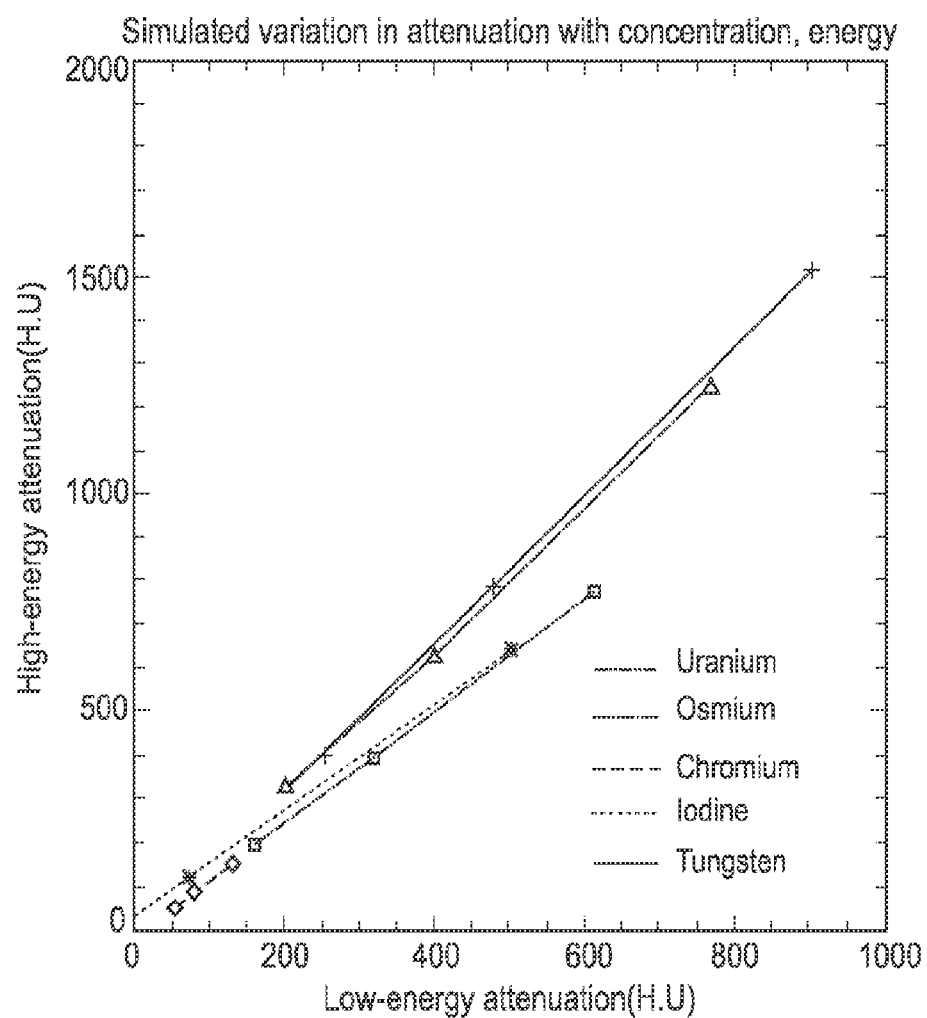
FIG. 10 is another plot of attenuation for a "low-energy" image and a "high-energy" image, in accordance with an example.

Plotting the average low- and high-energy voxel values in a central ROI for the different tube concentration values results in the graph 704 as shown. The graph 704 illustrates that there is a clear separation between iodine and tungsten in this dual-energy space. Such plots may be used in dual-energy CT to generate material-specific classifiers that can be used to assign unknown voxels in a subsequent image to one of two materials. Simulations with the same scintillator structure and a typical tube spectrum (which is more peaked than a synchrotron spectrum) suggest that even better material separation will be possible in that context, as shown in FIG. 10. In any event, the plots demonstrate the feasibility of assembly two 'commodity' type scintillators to form a multi-layer scintillator that can distinguish multiple metal-based stains.

Other modifications will be apparent. For example, if the dichroic mirror unexpectedly contributes unacceptable loss or spherical aberrations, a single objective lens coupled to a color scientific CCD can be used.

While various techniques may be used to determine a desired scintillator thickness, in some examples a signal-to-noise ratio (SNR) vs. thickness may be plotted and used. For example, the noise in the measurements in each detector layer will follow an approximately Gaussian distribution (the energy weighting precludes strictly Poisson noise) with mean $\mu_j = M_j$ and variance $$\sigma_j^2 = \left[\frac{\eta_{col}\eta_{x/v}^j}{E_v^j}\right]^2 \int E^2 S_j(E) \exp\left\{-\sum_{i=1}^{N} A_i f_i(E)\right\} dE. \quad (Eq.\ 13)$$

The Cramer Rao lower bound states that the variance in the estimate of the $i_{th}$ basis function line integral is greater than or equal to the $i_{th}$ diagonal of the inverse Fischer information matrix, which is given by $$\mathcal{F}_{\alpha\beta} = \sum_{j=1}^{M} \frac{1}{\sigma_j^2} \frac{\partial \mu_j}{\partial A_\alpha} \frac{\partial \mu_j}{\partial A_\beta} + \frac{1}{2} \frac{1}{\sigma_j^4} \frac{\partial \sigma_j^2}{\partial A_\alpha} \frac{\partial \sigma_j^2}{\partial A_\beta}. \quad (Eq.\ 14)$$

From this the SNR may be determined versus scintillator thickness allowing designers to choose an optimum thickness for a desired SNR value, or optimum set of thicknesses. For example, designers can choose a single layer thickness and target material that gives the best SNR performance across a range of integrated concentrations of the stains, while identifying optimal choices of kVp and tube filtration to use in a given concentration regime (i.e., for a smaller or more lightly stained fish).

While osmium and uranium were used in the above examples, any number of heavy metal stains may be used, including for example among those used in electron microscopy. An example listing of heavy metal stains and their staining targets are listed in Table 5. These stains were chosen in part because of their ability to be used in wholemount organisms and because of the existence of a K-edge or L-edge between 10 and 35 keV, which was a targeted operating range for some example implementations.

TABLE 5

Potential heavy metal stains

| Stain | Abbrev. | Biological target | Abs. edge |
|---|---|---|---|
| Osmium Tetroxide | $OsO_4$ | Lipids, cell membranes | 10.87 keV |
| Uranyl Acetate | UA | General (nucleic acids) | 17.17 keV |
| Phosphotungstic acid | PTA | Fibrin, collage, connective tissue | 10.20 keV |
| Phosphomolybdic acid | PMA | Connective tissue | 19.99 keV |
| Lugol's iodine | IKI | Cell nuclei | 33.16 keV |
| Silver nitrate | AgN | Proteins, DNA, reticula | 25.51 keV |
| Lead acetate | PbA | General, nonspecific | 13.03 keV |
| Indium chloride | InC | Nucleic acids | 27.94 keV |

Various examples are discussed herein applying the techniques to zebrafish. However, it is noted the present techniques may be applied to any pathology sample that includes biologic targets, including, but not limited to lipids, cell membranes, general targets such as nucleic acids, fibrin, collagen, connective tissue, cell nuclei, proteins, DNA, and reticula. The samples may be ex vivo samples of tissue, for example, human, mammalian, or non-mammalian tissue removed from a host body, organ, or other tissue sample. While in other examples, the sample may be examined in vivo.

The imaging and image analysis operation of the techniques herein may be performed on a computer system, for example, coupled to the optical detectors described herein and containing an imaging processor that collect images of the different stained biologic targets and produces a 3D color X-ray image of the sample. The computer system can be part of a computed tomography (CT) imaging system, for example. That computer system may include a computing device in the form of a computer which may be a personal computer, a server, a router, a network PC, a peer device or other common network node device. That computer may include subsystems such as, but not limited to, a processing unit, a system memory, and a system bus that couples various system components including the system memory to the processing unit. The system bus may be any of several types of bus structures including a memory bus or memory controller, a peripheral bus, and a local bus using any of a variety of bus architectures.

Such computer system would typically include a variety of computer readable media. Computer readable media can be any available media that can be accessed by computer and includes both volatile and nonvolatile media, and both removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, hard disk, magnetic cassettes, magnetic tape, magnetic disk storage or other magnetic storage devices, or any other medium which can be used to store the desired information and which can accessed by computer. For example, a hard disk drive is typically connected to the system bus through a non-removable memory interface such as interface, and magnetic disk drive and optical disk drive are typically connected to the system bus by a removable memory interface, such as an interface.

The drives and their associated computer storage media provide storage of computer readable instructions, data structures, program modules and other data for the computer. For example, a hard disk drive may store an operating system, application programs, other program modules, and program data. A user may enter commands and information into the computer through input devices such as a keyboard and cursor control device, commonly referred to as a mouse, trackball or touch pad.

One or more monitors or other type of display device may be connected to the system via an interface, such as a graphics controller, and used to display 2D or 3D x-ray images among other things for example. In addition to the monitors, computers may also include other peripheral output devices such as printer, which may be connected through an output peripheral interface.

The computer system may operate in a networked environment using logical connections to one or more remote computers, such as a remote computer. The remote computer may be a personal computer, a server, a router, a network PC, a peer device or other common network node, and typically includes many or all of the elements described above relative to the computer. The logical connections include a local area network (LAN) and a wide area network (WAN), but may also include other networks. Such networking environments are commonplace in hospitals, offices, enterprise-wide computer networks, intranets and the Internet.

Another computer system having like elements may be used to control operation of the x-ray source. For example, an X-raying imaging system computer may control an X-ray source to provide multiple illuminations of a sample at a plurality of monochromatic X-ray illumination energies or at a plurality of polychromatic X-ray illumination energies. The X-ray imaging system computer may control single illumination of polychromatic X-ray illumination energies. Thus, all aspects of X-ray source output control may be provided through a computer system; and that computer system may be a dedicated computer system or combined with the imaging processing image system discussed above.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

Thus, although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. An apparatus for imaging biologic targets within a sample, the apparatus comprising:
   an X-ray source configured to produce a X-ray energy;
   the sample positioned to receive the X-ray energy, the sample containing a plurality of biologic specific stains each staining a different biologic target within the sample;
   an X-ray responsive substrate configured to produce an output corresponding to the plurality of biologic specific stains within the sample; and
   an imaging stage configured to produce, from the output of the X-ray responsive substrate, a plurality of images, wherein each image is of a different one of the stained biologic targets within the sample, wherein the imaging stage is configured to produce the plurality of images using an energy decomposition model, and wherein the imaging stage is configured to combine the plurality of images resulting from the energy decomposition model into a fused image.

2. The apparatus of claim 1, wherein the X-ray energy comprises multiple illuminations at a plurality of monochromatic X-ray illumination energies chosen to target the plurality of biological stains.

3. The apparatus of claim 2, where the plurality of monochromatic illumination energies comprises two or three different X-ray energies.

4. The apparatus of claim 3, wherein the plurality of illumination energies are selected from the group consisting of 9.3 keV, 13.8 keV, 18.5 keV, and 22.5keV.

5. The apparatus of claim 1, wherein the X-ray energy comprises multiple illuminations at a plurality of polychromatic X-ray illumination energies chosen to target the plurality of biological stains.

6. The apparatus of claim 1, wherein the X-ray energy comprises single illumination at a polychromatic X-ray illumination energy chosen to target the plurality of biological stains.

7. The apparatus of claim 1, wherein the X-ray responsive substrate is configured to produce a different wavelength optical output for each of the plurality of biologic specific stains within the sample, and wherein the X-ray responsive substrate is a scintillator formed of multiple X-ray responsive layers, each layer responsive to a different range of incident X-ray energies to produce a different wavelength optical output.

8. The apparatus of claim 7, wherein the scintillator comprises two X-ray responsive layers and a substrate layer.

9. The apparatus of claim 7, wherein the scintillator comprises more than two X-ray responsive layers.

10. The apparatus of claim 7, wherein the scintillator is single layer scintillator.

11. The apparatus of claim 7, wherein the biologic specific stains are heavy-metal stains.

12. The apparatus of claim 7, wherein the biologic specific stains are selected from the group consisting of osmium tetroxide, uranyl acetate, phosphotungstic acid, phosphomolybdic acid, Lugol's iodine, silver nitrate, lead acetate, and indium chloride.

13. The apparatus of claim 7, wherein the biologic targets are selected from the group consisting of lipids, cell membranes, general targets such as nucleic acids, fibrin, collagen, connective tissue, cell nuclei, proteins, DNA, and reticula.

14. The apparatus of claim 7, wherein each of the multiple X-ray responsive layers is between 1 micron and 1 cm in thickness.

15. The apparatus of claim 7, wherein each of the multiple X-ray responsive layers is between 5 microns and 500 microns in thickness.

16. The apparatus of claim 7, wherein each of the multiple X-ray responsive layers is between 5 microns and 50 microns in thickness.

17. The apparatus of claim 7, wherein the imaging stage comprises at least one focusing lens stage and micron-sized computed tomography sensor.

18. The apparatus of claim 7, wherein the imaging stage comprises a plurality of focusing lens stage and micron-sized computed tomography sensor pairs, one for each of the different wavelength optical outputs.

19. The apparatus of claim 17 or 18, further comprising an imaging processor to collect a plurality of the images of the different stained biologic targets from the imaging stage and produce a 3D color X-ray image of the sample.

20. The apparatus of claim 1, wherein the plurality of biologic specific stains comprise a pair of heavy metal stains, wherein the heavy metals for the pair are selected from the group consisting of osmium, uranium, iodine, molybdenum, lead, and tungsten and selected to minimize signal noise in the image of each of the different stained biologic targets within the sample.

21. The apparatus of claim 1, wherein the sample is positioned on rotating stage and to rotate relative to the X-ray source during illumination by the X-ray energy.

22. A method of X-ray imaging and discriminating biologic targets within a sample, the method comprising:
staining the sample with a plurality of biologic specific stains each staining a different one of the biologic targets within the sample;
dynamically illuminating the stained sample with X-ray energy;
collecting, into an X-ray responsive substrate, output X-ray energy from the illuminated sample, where that output X-ray energy from the illuminated sample is formed of different X-ray energy regions corresponding to the different biologic specific stains; and
imaging each of the biologic targets to produce a plurality of images based on output from the X-ray responsive substrate corresponding to the plurality of biologic specific stains within the sample, wherein the each image corresponds to a different biologic specific stain, and wherein the imaging comprises producing the images using an energy decomposition model and combining the images resulting from the energy decomposition model into a fused image.

23. The method of claim 22, wherein the X-ray responsive substrate configured to produce a different wavelength optical output for each of the plurality of biologic specific stains within the sample, and wherein the X-ray responsive substrate is formed of multiple X-ray responsive layers, each layer responsive to a different one of the X-ray energy regions to collectively produce a different wavelength optical output for each of the plurality of biologic specific stains within the sample.

24. The method of claim 22, wherein dynamically illuminating the stained sample with X-ray energy comprises illuminating the sample with multiple illuminations at a plurality of monochromatic X-ray illumination energies chosen to target the plurality of biological stains.

25. The method of claim 24, where the plurality of monochromatic X-ray illumination energies comprises two or three different X-ray energies.

26. The method of claim 25, wherein the plurality of monochromatic illumination X-ray energies are selected from the group consisting of 9.3keV, 13.8 keV, 18.5 keV, and 22.5 keV.

27. The method of claim 22, wherein dynamically illuminating the stained sample with X-ray energy comprises illuminating the sample with a plurality of polychromatic X-ray illumination energies chosen to target the plurality of biological stains.

28. The method of claim 22, wherein dynamically illuminating the stained sample with X-ray energy comprises illuminating the sample with a single illumination at a polychromatic X-ray illumination energy chosen to target the plurality of biological stains.

29. The method of claim 22, further comprising combining the images of each of the biologic targets to produce a 3D color X-ray image of the sample.

30. The method of claim 22, wherein staining the sample with a plurality of biologic specific stains comprises staining the sample with a plurality of heavy-metal stains selected from the group consisting of osmium tetroxide, uranyl acetate, phosphotungstic acid, phosphomolybdic acid, Lugol's iodine, silver nitrate, lead acetate, and indium chloride.

31. The method of claim 22, wherein staining the sample with a plurality of biologic specific stains comprises staining the sample with a plurality of heavy-metal stains, wherein the heavy metals are selected from the group consisting of osmium, uranium, iodine, molybdenum, lead, and tungsten.

32. The method of claim 22, wherein staining the sample with a plurality of biologic specific stains comprises using a pair of heavy metal stains, wherein the heavy metals for the pair are selected from the group consisting of osmium, uranium, iodine, molybdenum, lead, and tungsten and selected to minimize signal noise in the image of each of the different stained biologic targets within the sample.

33. The method of claim 22, wherein dynamically illuminating the stained sample comprises rotating the stained sample during illumination.

* * * * *

UNITED STATES PATENT AND TRADEMARK OFFICE
CERTIFICATE OF CORRECTION

PATENT NO. : 9,513,233 B2  
APPLICATION NO. : 14/354855  
DATED : December 6, 2016  
INVENTOR(S) : Patrick La Riviere et al.

It is certified that error appears in the above-identified patent and that said Letters Patent is hereby corrected as shown below:

In the Specification

Column 1, Line 3, immediately after the title, please insert:

--STATEMENT OF GOVERNMENT INTEREST

This invention was made with government support under Grant Nos. RR017041 and OD011152, awarded by the National Institutes of Health. The Government has certain rights in the invention.--

Signed and Sealed this
Fourth Day of April, 2017

Michelle K. Lee
*Director of the United States Patent and Trademark Office*